United States Patent [19]
Urban

[11] Patent Number: 5,637,713
[45] Date of Patent: Jun. 10, 1997

[54] PROCESS FOR PREPARING TRANS-PIPERIDINE-2,5-DICARBOXYLATES

[75] Inventor: Frank J. Urban, Waterford, Conn.

[73] Assignee: Pfizer Inc., New York, N.Y.

[21] Appl. No.: 542,270

[22] Filed: Oct. 12, 1995

Related U.S. Application Data

[62] Division of Ser. No. 217,532, Mar. 24, 1994, Pat. No. 5,489,688, which is a division of Ser. No. 104,153, filed as PCT/US92/00029 Jan. 8, 1992, Pat. No. 5,326,874.

[51] Int. Cl.$^6$ .................................................. C07D 211/60
[52] U.S. Cl. ........................................................ 546/227
[58] Field of Search ............................................ 546/227

[56] References Cited

U.S. PATENT DOCUMENTS

| | | | |
|---|---|---|---|
| 4,018,767 | 4/1977 | Buyniski et al. | 546/700 |
| 4,505,911 | 3/1985 | Dolak et al. | 546/200 |

FOREIGN PATENT DOCUMENTS

| | | |
|---|---|---|
| 0057092 | 8/1982 | European Pat. Off. . |
| 0380217 | 8/1990 | European Pat. Off. . |

OTHER PUBLICATIONS

Yamada et al., J. Org. Chem., v. 48, pp. 843–846 (1983).
Mastafanova et al., Chem. Heterocyclic Compounds, Translated from Russian, v. 21, pp. 305–309 (1985).
J. Am. Chem. Soc., v. 97, No. 1, 159–167 (1975).
Chem. Abstr., v. 103, No. 23, 1985, Mastafanova et al., Abst. No. 195965u.
Chem. Abstr., v. 107, No. 7, 1987, Kuleshova et al., Abstr. No. 58343h.
Prestridge et al., J. Org. Chem., V. 40 (22), 3287, (1987).
Albert et al., Syntheses, 635, 1987.

*Primary Examiner*—C. Warren Ivy
*Assistant Examiner*—Raymond Covington
*Attorney, Agent, or Firm*—Peter C. Richardson; Gregg C. Benson; James T. Jones

[57] ABSTRACT

Process for the preparation of a dialkyl trans-piperidine-2,5-dicarboxylate from a corresponding dialkyl cis-piperidine-2,5-dicarboxylate via a trans-substituted pyridine derivative of the formula

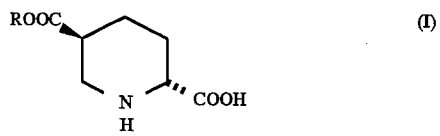

(I)

wherein R is a $(C_1-C_3)$alkyl group.

16 Claims, No Drawings

PROCESS FOR PREPARING TRANS-PIPERIDINE-2,5-DICARBOXYLATES

This is a division of application Ser. No. 08/217,532 filed on Mar. 24, 1994, U.S. Pat. No. 5,489,688 which is a division of application Ser. No. 08/104,153 filed on Aug. 20, 1993, now U.S. Pat. No. 5,326,874, which was filed under 35 USC 371 based on PCT/US92/00029 filed internationally on Jan. 8, 1992 claiming priority from U.S. application Ser. No. 07/661,726 filed Feb. 27, 1991.

BACKGROUND OF THE INVENTION

The present invention is directed to processes for the preparation of a dialkyl trans-piperidine-2,5-dicarboxylate via a trans substituted piperidine derivative of the formula

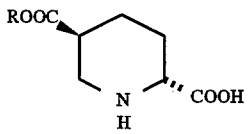

wherein R is $(C_1-C_3)$alkyl. Said trans-piperidine derivatives are particularly useful as intermediates in the synthesis of certain neuroleptic, racemic or optically active perhydro-1H-pyrido[1,2-a]pyrazines having the relative stereochemical formula:

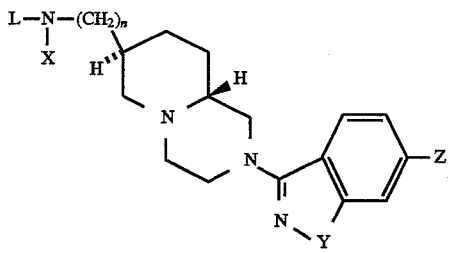

wherein

Z is H or Cl;

Y is O or S;

n is 1, 2, 3 or 4; and

L and X are taken separately, X is H or $(C_1-C_2)$alkyl and L is $R^a(CH_2)_mCO$ where m is 0, 1, 2 or 3 and $R^a$ is $(C_1-C_6)$alkyl, $(C_3-C_7)$cycloalkyl, phenyl, naphthyl, furyl, benzofuranyl, thienyl, benzothienyl, pyrrolyl, indolyl, isoindolyl or one of said groups substituted on aromatic or heteroaromatic ring with fluoro, chloro, $(C_1-C_2)$alkyl or $(C_1-C_2)$alkoxy; or L and X are taken together and are:

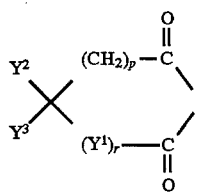

where $Y^1$ is $CH_2$, S, O or NH; $Y^2$ and $Y^3$ are taken separately and $Y^2$ and $Y^3$ are each independently hydrogen or methyl, or $Y^2$ and $Y^3$ are taken together and are $(CH_2)_q$; p is 1 or 2; q is 2, 3, 4 or 5; and r is 0 or 1;

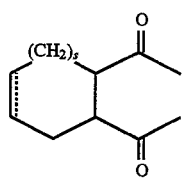

where s is 0 or 1; and—represents a bond or no bond;

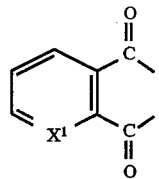

where $X^1$ is CH or N;

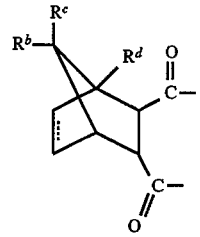

where $R^b$, $R^c$ and $R^d$ are each independently H or $CH_3$ and—represents a bond or no bond;

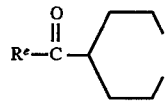

where $R^e$ is phenyl or phenyl substituted with F, Cl, $(C_1-C_2)$alkyl or $(C_1-C_2)$alkoxy;

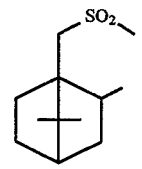

or a pharmaceutically acceptable acid addition salt thereof.

The compounds of the formula (A), their preparation and their utility as antipsychotics are fully described herein and in concurrently filed U.S. patent application Ser. No. 07/661,791 by Bright et al., for "Perhydro-1H-pyrido[1,2-a] pyrazine Derivatives Having Neuroleptic Activity."

Dimethyl trans-piperidine-2,5-dicarboxylate has been previously prepared by Mastafanova et al., Chemistry of Heterocyclic Compounds-Translated from Russian, v. 21, pp. 305–309 (1985), via trans-piperidine-2,5-dicarboxylic acid which was in turn obtained as an equilibrium mixture with cis-piperidine-2,5-dicarboxylic acid by prolonged heating of the cis-isomer at 200° C. in a high pressure bomb in the presence of excess aqueous sodium hydroxide.

Yamada et al., J. Org. Chain., v. 48, pp. 843–846 (1983), have described a method for the racemization of optically active alpha-amino acids in which the amino acid is heated in a carboxylic acid (e.g., formic, acetic, or propionic acid) in the presence of an aliphatic or aromatic aldehyde.

SUMMARY OF THE INVENTION

We have now found that dialkyl cis-piperidinedicarboxylates can be equilibrated with the corresponding trans-isomer under mild conditions in the presence of an aliphatic or aromatic aldehyde (such as those noted above) in a carboxylic acid as solvent. This equilibration is accompanied by concurrent hydrolysis of the ester group at the 2-position of the piperidine ring. This is most fortuitous, since this acid is amenable to optical resolution via a diastereomeric salt with an optically active amine. Such optically active acids permit the highly efficient synthesis of those above-noted neuroleptic compounds which are optically active.

The present invention is specifically directed to the trans-substituted piperidine of the above formula (I). For its ease of preparation, the preferred compound is that wherein R is methyl.

The present invention is further directed to a process of preparing said trans-substituted piperidine of the formula (I) which comprises contacting a corresponding cis-substituted piperidine derivative of the formula

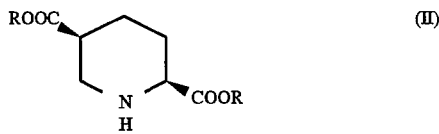

wherein R is defined as above, with an aldehyde in a carboxylic acid $R^1COOH$, wherein $R^1$ is hydrogen or $(C_1–C_3)$alkyl; and separating said trans derivative of the formula (I) from the resulting mixture.

The present invention is also directed to a process for the preparation of a trans-piperidine derivative of the formula

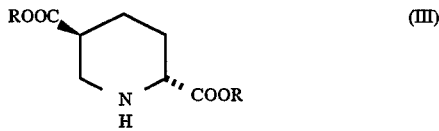

wherein R is $(C_1–C_3)$alkyl, which comprises the steps of:

(a) contacting a corresponding cis-substituted piperidine derivative of the formula

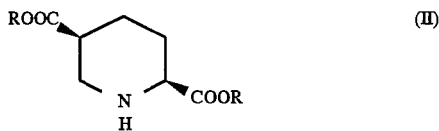

wherein R is defined as above, with an aldehyde in a carboxylic acid $R^1COOH$, wherein $R^1$ is hydrogen or $(C_1–C_3)$alkyl, to form a mixture of cis and trans compounds of the formulas

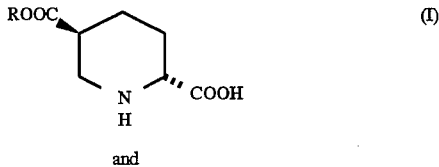

and

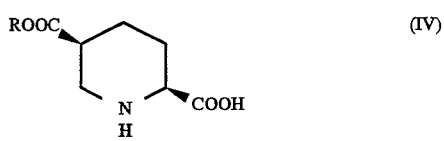

(b) conventionally esterifying said mixture of compounds of the formulae (I) and (IV) to form a mixture of said trans and cis derivatives of the above formulas (II) and (III); and (c) separating said trans derivative of the formula (II) from the mixture.

According to either of these processes, the preferred value of each of R and $R^1$ is methyl; and the preferred aldehyde is salicylaldehyde.

The present invention is also directed to compounds of the formula

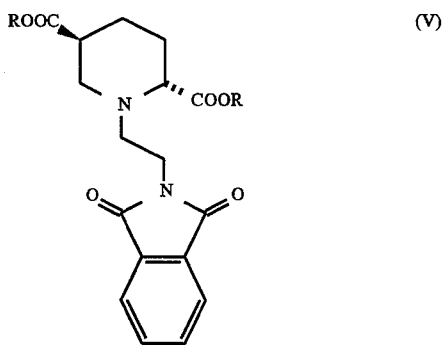

wherein R is as defined above, which are particularly valuable intermediates in the preparation of the above compounds of the formula (A).

DETAILED DESCRIPTION OF THE INVENTION

The present invention is readily carried out. Accordingly, a dialkyl cis-piperidine-2,5-dicarboxylate is contacted with a catalytic quantity of an aliphatic or aromatic aldehyde in an excess of a carboxylic acid, as defined above, which generally also serves as solvent, so as to form an equilibrium mixture of cis- and desired trans-piperidine monoesters, of above formulas (IV) and (I), respectively.

The structure of the aldehyde is not critical. Suitable aldehydes include, but are not restricted to, formaldehyde, acetaldehyde, propionaldehyde, n-butyraldehyde, n-heptaldehyde, acrolein, benzaldehyde, salicylaldehyde, p-hydroxybenzaldehyde, p-anisaldehyde, o-nitrobenzatdehyde, 5-nitrosalicylaldehyde, furfural, and so forth. In the present instance, salicylaldehyde is a preferred aldehyde, since it leads relatively rapidly to the desired equilibrium mixture of cis- and trans-5-(alkoxycarbonyl)piperidine-2-carboxylic acids (IV and I, respectively). The quantity of aldehyde is not critical, but will generally be in the range of about 0.05 to 0.5 molar equivalents, a level which is generally sufficient to achieve equilibrium within a reasonable period of time. The particular carboxylic acid used is likewise not critical. However, because of its ready availability, acetic acid is preferred. The temperature at which equilibrium is achieved is likewise uncritical, but is preferably in the range of about 70°–120° C., high enough to achieve equilibrium within a reasonable period of time, but not so high as to cause an undue level of byproducts and decomposition.

Once equilibrium has been achieved, the product mixture of cis-trans-isomers can be separated by conventional methods into the desired trans-acid of formula (I) and cis-acid of formula (IV). The former is further used in the preparation of compounds of formula (A) depicted above. The recovered cis-isomer, which need not be free of (trans-isomer, is suitable for recycling in place of the cis-diester starting material. In the preferred synthetic route for the conversion of trans-acid (I) to the compounds of the formula (A), the first step is conversion of said trans-acid to the trans-diester (III), using conventional methods of esterification.

Alternatively, the mixture of cis- and trans- acids, (I) and (IV), are re-esterified by conventional methods, and the resulting cis- and trans-diesters, (II) and (III), then separated by conventional methods. The trans-diester is then used in the synthesis of the compounds of the formula (I), and the cis-diester recycled into additional trans-acid (I) or trans-diestar (III).

In the preferred synthetic route for the conversion of trans-diester to the compounds of the above formula (A), the piperidine diestar (III) is initially converted to the N-(2-(phthalimido)ethyl) derivative of the formula (V), readily accomplished by the action of 2-(phthalimido)ethyl triflate ester (at least one molar equivalent, usually in 10–20% molar excess). This reaction is generally carried out in a biphasic reaction inert solvent system such as methylene chloride and water in the presence of a 2–3 molar excess of a base such as $Na_2CO_3$ which is soluble in the aqueous phase. Temperature is not critical, temperatures in the range of about 5°–45° C. being generally satisfactory, with the use of ambient temperature (e.g., 16°–26° C.) being particularly convenient.

The compound (V) is then further converted, by a multiplicity of chemical steps, to the antipsychotic compounds of the formula (A). These transformations are extensively exemplified below.

All clinically effective antipsychotic agents share one activity, the blockade of dopamine binding to D-2 receptors. Although the standard antipsychotics interact with a wide variety of neurotransmitter receptors, their potency in blocking D-2 binding is the only activity which shows a highly significant correlation with their oral clinical dosage (Creese et al., Science, 192: 481–483, 1976). This clinical effect is believed to result from actions on mesolimbic-mesocortical dopamine projections to the forebrain, specifically inhibition of dopamine hypersensitivity caused by increased receptor density, as demonstrated in post-mortem studies of schizophrenic brains (Lee et al., Nature, 274: 897, 1978).

The relative ability of the above compounds of the formula (A) to displace binding at the D-2 receptors was determined according to standard radioligand homogenate binding techniques, as follows. Adult, male Sprague-Dawley rats (3 per assay) were decapitated, the brains quickly removed and caudate-putamen was dissected out. Tissue was homogenized in 50 volumes of ice-cold 50 mM Tris-HCl buffer containing 100 mM NaCl and 1 mM $MgCl_2$ and adjusted to pH 7.2. This mixture was centrifuged twice at 20,000 xg for 15 minutes each, the supernatent being discarded each time and the pellet resuspended in fresh buffer with homogenization. The final pellet was resuspended in buffer to a concentration of 5.6 mg/ml. This tissue suspension was then added to tubes containing a fixed concentration of 3H-spiroperidol (0.2 nM), and various concentrations of test drug. Other tubes contained only buffer ("total") or a saturating concentration of (+)butaclamol (10 mM="blank"). The tubes (final volume—1.0 ml) were incubated at 37° C. for 15 minutes, then rapidly filtered under vacuum through glass fiber filters and rinsed with 12 ml of ice-cold buffer in a Brandel Cell Harvester. The filters were then removed and counted in a scintillation counter using 5 ml of Beckman ReadySafe scintillation fluid. The resulting counts were then used to generate the $IC_{50}$, or extrapolated concentration of test drug necessary to inhibit one-half of the binding, for each compound in question. (Method of Laysen et al., Biochemical Pharmacology, 27: 307–316 (1978).

The antipsychotic activity of the compounds of the formula (A)is also demonstrated by their neuroleptic activity using methods based on standard procedures. In one method, adult male Sprague-Dawley rats are pretreated with appropriate doses of the test compound by subcutaneous injection. One half hour later, all rats are injected intraperitoneally with 1 mg/kg apomorphine hydrochloride dissolved in an 0.1% ascorbate solution. The rats are rated behaviorally according to the following scale at 5, 15, 25, 35 and 45 minutes after the apomorphin injection: 0=alert but not moving, 1=moving about the cage, 2=discontinuous sniffing behavior, 3=continuous sniffing with discontinuous oral movements, and 4=continuous licking and chewing movements.

The biological activity of the compounds of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive aggression, tension and social or emotional withdrawal in psychotic patients.

A compound of formula (A), or a pharmaceutically acceptable salt thereof, is administered to a human subject either alone, or, preferably, in combination with pharmaceutically acceptable carriers or diluents, in a pharmaceutical composition, according to standard pharmaceutical practice. These compositions are administered orally or parenterally. Parenteral administration includes especially intravenous and intramuscular administration. Additionally, in a pharmaceutical composition comprising a compound of formula (A), or a pharmaceutically acceptable salt thereof, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of a neuroleptic agent, the compounds of the formula (A) are administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When an agent of this invention is to be used in a human subject to treat a psychotic disorder, the daily dosage will normally be determined by the prescribing physician.

Moreover, the dosage will vary according to the age, weight and response of the individual patient as well as the severity of the patient's symptoms. However, in most instances, an effective amount for treating a psychotic disorder will be a daily dosage in the range from about 1 to 500 mg, preferably about 5 to 100 mg, in single or divided doses, orally or parenterally. In some instances it may be necessary to use dosages outside these limits.

The following examples are provided solely for the purpose of further illustration.

EXAMPLE 1 trans-5-(Methoxycarbonyl)-piperidine-2-carboxylic Acid

Dimethyl cis-piperidine-2,5-dicarboxylate (20 g, 0.077 mol), salicylaldehyde (3 ml, about 0.014 mol) and acetic acid (200 ml) were combined and heated at reflux for 24 hours. The mixture was cooled and stripped in vacuo to a thick oil. This residue was taken up in 300 ml of isopropyl alcohol and restripped to 200 ml, by which time product began to precipitate. After granulating for 2 hours, title product was recovered by filtration and air dried, 9.20 g; m.p. 184° C. (softening), 191°–200° C. (dec.); $^1$H-NMR (CDCl$_3$, 300 MHz)delta: 3.73 (s, 3H), 3.62 (septet, 2H), 3.15 (t, 1H), 2.90 (m, 1H), 2.30 (m, 2H), 1.74 (m, 2H).

Crude cis-5-(methoxycarbonylpiperidine-2-carboxylic acid, containing some additional trans-isomer, 4.52 g, was recovered by stripping mother liquors. This material is suitable for recycling in the present process in place of dimethyl cis-piperidine-2,5-dicarboxylate.

Substitution of benzaldehyde for salicylaldehyde gave the same products, but the desired equilibrium mixture of cis and trans acids was achieved more slowly.

EXAMPLE 2

3:1 Mixture of trans and cis-5-(Methoxy-carbonyl) piperidine-2-carboxylic Acid Dimethyl cis-piperidine-2,5-dicarboxylate (112 g, 0.56 mol), salicylaldehyde (3 ml, 0.056 mol) and glacial acetic acid (600 ml) were combined and the resulting mixture heated at about 100° C. for 60 hours. The mixture was cooled, than stripped in vacuo to a thick oil from which 61.7 g (59%) of title products crystallized upon stirring with 800 ml of isopropyl alcohol. Product ratio was determined by $^1$H-NMR (D$_2$O, 300 MHz), a peak at 3.13 ppm (t, 1H, J=14.5 Hz)being diagnostic of trans, and a peak at 3.33 ppm (dd, 1H) being diagnostic of cis.

EXAMPLE 3

Dimethyl trans-Piperidine-2,5-dicarboxylate Hydrochloride

Method A

Title product mixture of the preceding Example (15.1 g, 0.08 mol) was suspended in 200 ml of methanol and stirred under N$_2$ at 0°–5° C. Thionyl chloride (7.35 ml, 0.1 mol) was added dropwise over about 5 minutes. After 30 minutes the mixture was warmed to room temperature, and after 1 hour warmed to reflux for 6 hours. Upon cooling title product (6.8 g) crystallized from the reaction mixture. A second and third crop (5.3 g and 0.63 g) were obtained by stripping mother liquors to low volume and diluting to 200 ml with isopropyl alcohol. The combined yield of present title product was 67%; m.p. 207°–209° C.

Analysis calculated:
C, 45.48; H, 6.79; N, 5.89.
C, 45.34; H, 6.55; N, 5.82.
Found:
Dimethyl cis-piperidine-2,5-dicarboxylate recoverable from mother liquors is recycled as starting material in Example 1 or 2 above.
Method B
In like manner, title product of Example 1 is converted to present title product.

EXAMPLE 4

Racemic Dimethyl trans-1-(2-(Phthalimido)-ethyl) piperidine-2,5-dicarboxylate To a well-stirred bi-phasic mixture consisting of sodium carbonate (500 g, 4.72 mol) in water (3 liters) and trans-2, 5-piperidine dicarboxylate dimethyl ester hydrochloride (280 g, 1.18 mol in methylene chloride (4.5 liters), a solution of 2-phthalimido-ethyl triflate (417 g, 1.29 mol) in methylene chloride (3 liters) was added in a steady stream over a 3 hour period. The organic layer was separated, and the aqueous layer was extracted with fresh methylene chloride (3 liters). The combined organic extracts were washed with water (3 liters), then with brine (3 liters), dried with anhydrous magnesium sulfate and finally, concentrated in vacuo to a solid. The entire residue was triturated in resulting ether (3 liters), with vigorous stirring, for 15 minutes. After cooling to ambient temperature, the solution was poured into hexanes (3 liters), and the resulting mixture was stirred for 18 hours. The resulting colorless solid was collected by filtration, and the filter cake was washed with hexanes (1 liter). In vacuo drying afforded 437.3 g (99.1% yield) of the title compound as a colorless solid. TLC Rf (ethyl acetate/methylene chloride=1:1 in volume; iodoplatinate spray): 0.5.

EXAMPLE 5

Racemic Methyl (7R*,9aS*)-4,6,7,8,9,9a-Hexahydro-2H,3H-pyrido[1,2-a]-pyrazin-1-one-7-carboxylate To a well-stirred suspension of the title product of Example 4 (194 g, 0.52 mol in methanol (3 liters), hydrazine monohydrate (57.1 g, 1.14 mol) was added. The reaction mixture was then stirred for 18 hours at ambient temperature. Methylene chloride (2 liters) was added, and the resulting mixture was vigorously stirred for 1 hour. The resulting white solids were filtered, and the filtercake was washed with methylene chloride (1 liter) before being discarded. In vacuo concentration of the filtrate afforded a colorless solid, which was granulated and then vigorously stirred in refluxing methylene chloride (3 liters) for 10 minutes. The cooled mixture was filtered, and the resulting filtrate was concentrated in vacuo to afford present title compound (89.4 g, 81.6% yield) as an ivory solid. TLC Rf (methylene chloride/methanol=9:1 in volume; iodoplatinate spray): 0.38.

EXAMPLE 6

Racemic (7R*,9aS*)-Perhydro-7-(hydroxymethyl)-1H-pyrido[1,2-a]pyrazine

To a stirred slurry of the amide-ester title product of Example 5 (244 g, 1.15 mol) in anhydrous tetrahydrofuran (THF, 5.5 liters), a 1.0M solution of lithium aluminum hydride (2.33 liters, 2.33 mol) was added dropwise under nitrogen while maintaining the temperature of the reaction mixture below 40° C. The mixture was then heated at reflux for 18 hours. After cautious dropwise addition of water (90 ml) to the reaction (cooled to ambient temperature) followed by the addition of 15% aqueous sodium hydroxide (90 ml) and finally, more water (270 ml), the mixture was stirred for 1 hour. Insoluble inorganic salts were removed by filtration, and the resulting filtrate was concentrated in vacuo to afford present title compound as a light yellow solid (179.4 g, 90.6% yield), sufficiently pure for use in the next step without further purification. TLC Rf (methylene chloride/methanol/concentrated aqueous ammonia=3:1:0.1 in volume; iodoplatinate spray): 0.19.

EXAMPLE 7

Racemic (7R*,9aS*)-2-(Benzo[d]isoxazol-3-yl)-perhydro-7-(hydroxymethyl)-1H-pyrido[1,2-a]pyrazine A stirred solution of alcohol-amine title product of Example 6 (179.4 g, 1.05 mol), 3-chloro-1,2-benzo[d]isoxazole (194.2 g, 1.26 mol), and 1,8-diazabicyclo[5.4.0]undec-7-ene (DBU, 197.9 g, 1.30 mol) in pyridine (400 ml) was heated at 100° C. for 18 hours. After cooling to 35° C., water (3 liters), methylene chloride (2.5 liters) and, finally, saturated aqueous sodium carbonate (2 liters) were added, and the resulting biphasic mixture was vigorously stirred for 3 hours. The tan solid precipitate which formed during the stirring period was filtered, and the filter cake was washed first with water and then with hexane (1 liter of each) prior to being dried in vacuo. Trituration of the entire sample (216 g) with isopropyl alcohol (630 ml) followed by filtration and in vacuo drying afforded present title compound (154.5 g, 51% yield) as a light tan powder, sufficiently pure for use in the next step without further purification. TLC Rf (methylene chloride/methanol=9:1 in volume; iodoplatinate spray): 0.50. $^{13}$CNMR (CDCl$_3$) delta 164.0, 161.1, 129.5, 122.3, 122.1, 116.2, 110.5, 66.3, 60.3, 58.7, 54.3, 53.7, 48.3, 39.1, 29.0, 26.7.

EXAMPLE 8

Racemic (7R*,9aS*)-2-(Benzo[d]isoxazol-3-yl)-perhydro-7-(methanesulfonyloxymethyl)-1H-pyrido[1,2-a]pyrazine To a chilled (5° C.) end stirred slurry of the alcohol title product of Example 7 (154.0 g, 0.54 mol) and triethylamine (81.76 ml, 59.6 g, 0.589 mol) in methylene chloride (3.0 liters), a solution of methanesulfonyl chloride (43.55 ml, 64.5 g, 0.563 mol) in methylene chloride (350 ml) was added dropwise ever 30 minutes. TLC monitoring (methylene chloride/methanol=9:1 in volume; iodoplatinate spray) of the reaction mixture after an additional ½ hour of stirring indicated incomplete reaction. Complete reaction was realized within ½ hour after addition of a second portion of triethylamine (8.23 ml, 6.0 g, 59.3 mmol) and methanesulfonyl chloride (4.32 ml, 6.4 g, 55.9 mmol) added dropwise as a methylene chloride (20 ml) solution. Water (3 liters) and methylene chloride (1.5 liters) were added, and the biphasic mixture was vigorously stirred prior to separation of the organic and aqueous phases. The aqueous portion was then extracted with a fresh portion of methylene chloride (1.5 liters). The organic extracts were then combined, washed with brine (twice with 2 liter portions) and dried over anhydrous sodium sulfate. Concentration in vacuo afforded the present title compound as a tan solid (178.0 g, 90.2% yield). TLC Rf (methylene chloride/methanol=9:1 in volume; iodoplatinate spray): 0.24. MS m/z 365.1 (M, C$_{17}$H$_{23}$N$_3$O$_4$S). $^{13}$CNMR (CDCl$_3$) delta 164.0, 160.9, 129.6, 122.4, 122.1, 116.0, 110.5, 71.9, 59.9, 57.7, 54.0, 53.3, 48.1, 37.4, 35.9, 28.4, 26.2.

EXAMPLE 9

Racemic (7S*,9aS*)-2-(Benzo[d]isoxazol-3-yl)-7-(cyanomethyl)perhydro-1H-pyrido[1,2-a]pyrazine A stirred solution of the mesylate title product of Example 8 (177.5 g, 0.486 mol) and sodium cyanide (35.7 g, 0.729 mol) in N,N-dimethylformamide (3.0 liters) was heated at 110° C. for 18 hours. The solvent was removed in vacuo, and the resulting tan solid residue was dissolved in a water/methylene chloride (2.5 liters of each) biphasic mixture. The pH of the weft-stirred mixture was adjusted to 10 (saturated aqueous sodium carbonate). The layers were then separated, and the aqueous phase was extracted with a fresh portion of methylene chloride (1.5 liters). The combined organic extracts were washed with brine (two 1 liter portions), dried over anhydrous sodium sulfate and concentrated in vacuo to afford present title compound as a tan solid (137.3 g, 95.3% yield). TLC Rf (ethyl acetate/hexane=1:1 in volume; iodoplatinate spray): 0.20. $^{13}$CNMR (CDCl$_3$) delta 164.0, 161.0, 129.6, 122.4, 122.0, 117.9, 116.0, 110.5, 59.9, 59.5, 53.9, 53.3, 48.1, 32.9, 29.6, 28.7, 22.1.

By the same method, the title mesylate product of Example 27 is converted to the corresponding nitrile, racemic(7R*,9aS*)-2-(Benzo[d]isoxazol3-yl)-7-(3-cyanopropyl)perhydro-1H-pyrido[1,2-a]pyrazine, also having 7 and 9a hydrogen substituents trans.

EXAMPLE 10

Racemic (7S*,9aS*)-7-(2-Aminoethyl)-2-(benzo[d]isoxazol-3-yl)perhydro-1H-pyrido[1,2-a]pyrazine To a stirred mixture of the nitrile title product of Example 9 (136.9 g, 0.462 mol) in anhydrous tetrahydrofuran (3.5 liters), a 1.0M solution of lithium aluminum hydride (LAH) in tetrahydrofuran (693 ml, 0.693 mol) was added dropwise over a 1 hour period. The reaction was heated at reflux for 6 hours, then stirred for 18 hours at ambient ternperature and, finally, quenched by cautious dropwise addition of water/tetrahydrofuran (26 ml and 30 ml respectively), 15 percent aqueous sodium hydroxide (26 ml), and water (80 ml). The mixture was stirred for 0.5 hour. Anhydrous sodium sulfate (400 g) was added, and the inorganic salts were filtered. The filter cake was washed with tetrahydrofuran (800 ml) and methylene chloride (1 liter). The washings were combined with the filtrate, and the resulting solution was concentrated in vacuo to afford the present title compound as a yellow solid (131.9 g, 95% yield). TLC Rf (methylene chloride/methanol/concentrated aqueous ammonia=9:1:0.1 in volume; iodoplatinate spray): 0.28. $^{13}$CNMR (CDCl$_3$) delta 164.0, 161.1, 129.4, 122.2, 122.1, 116.2, 110.4, 61.7, 60.2, 54.2, 53.8, 48.3, 39.7, 38.7, 33.9, 30.7, 29.4.

By the same method the 3-cyanopropyl substituted product of the preceding Example is converted to the corresponding 4-aminobutyl derivative, which in turn is converted to the corresponding imide derivatives by the methods of Examples 13–15.

EXAMPLE 11

Optically Active (7S,9aS)-7-(2-Aminoethyl)-2-(benzo[d]isoxazol-3-yl)perhydro-1H-pyrido[1,2-a]pyrazine Racemic title amine of Example 10 (131.5 g, 0.438 mol) was dissolved in refluxing ethanol (2.4 liters). S-(+)- mandelic acid (66.6 g, 0.438 mol) was added, affording a clear solution which was allowed to cool slowly and stand at ambient temperature for 18 hours. The colorless crystalline precipitate was filtered, and the cake was washed thrice with 300 ml portions of diethyl ether. in vacuo drying afforded 92.6 g of colorless crystalline (partially resolved) salt; m.p. 205°–210° C. The entire sample was then refluxed in ethanol (1.8 liters) for one hour, affording a solution-suspension which was filtered after being allowed to cool to ambient temperature. Washing of the filter cake with two 300 ml portions of diethyl ether followed by drying in vacuo afforded 75.6 of colorless crystalline salt; m.p. 214°–217° C., further progressed toward optical resolution and isolation of the 7S,9aS-(−)-enantiomer as its S-(+)-mandelic acid salt. Again, the entire sample was refluxed in ethanol (1.0 liter) for 0.5 hours, cooled to ambient temperature and allowed to stand for 18 hours. Filtration followed by diethyl ether-washing of the filter cake and in vacuo drying afforded 66.3 g of colorless crystals; m.p. 216°–218° C. The just-described crystallization procedure, utilizing 1 liter of ethanol as the crystallization solvent was repeated five more times to afford 45.1 g of resolved S-(+)-mandelic acid salt of the 7S,9aS-(−)-enantiomer; m.p. 223°–224° C. The entire sample was dissolved in a biphasic methylene chloride (2.5 liters)/water (1.4 liters) mixture with the pH adjusted to 9 (saturated aqueous sodium carbonate). The layers were separated, and the aqueous portion was extracted with 2 liters of fresh methylene chloride. Concentration in vacuo of the anhydrous sodium sulfate-dried combined organic extracts afforded present title compound (29.9 g, 45.4% yield) as a colorless amorphous solid. $[\alpha]_D^{20}$–865 (c=3.73, methylene chloride). $^{13}$CNMR (CDCl$_3$) delta: identical to that of the racemic amine.

Optical resolution of the racemic (+/−)-amine to the present 7S,9aS-(−)-amine was confirmed by $^{19}$FNMR comparative studies of its chiral Mosher amide derivative with the corresponding derivative of its 7R,9aR-(+)-counterpart (the product of Example 12), which were prepared by Preparations detailed below. Single crystal X-ray diffraction studies of these Mosher amide derivatives established their absolute stereochemistry.

EXAMPLE 12

Optically Active (7R,9aR)-7-(2-Amino-ethyl)-2-(benzo[d]isoxazol-3-yl)perhydro-1H-pyrido[1,2-a]pyrazine A solution of the title racemic amine of Example 10 (1.40 g, 3.79 mmol) and R-(−)-mandelic acid (577 mg, 3.79 mmol) in ethanol (24 ml) was allowed to stand at ambient temperature for 18 hours during which time a heavy crystalline mass formed. The crystalline solid was filtered, washed with diethyl ether and dried in vacuo (270 mg). The entire sample was dissolved in hot ethanol (5 ml). The solution was concentrated in vacuo to a volume of 4 ml and allowed to stand at ambient temperature for 18 hours to complete crystallization. The crystalline mass was filtered, washed with diethyl ether, and dried in vacuo to afford the R-(−)-mandelic acid salt of present title 7R,9aR-(+)-amine, 107 mg (12.5% yield); m.p. 218°–222° C.; $[\alpha]_D^{20}$–19.6 (c=0.56, methanol).

The entire sample was dissolved in a well-stirred methylene chloride/water (8 ml and 4 ml, respectively) mixture with the pH adjusted to 9.5 (saturated aqueous sodium carbonate). The separated organic extract was washed with an equal volume of water, dried (anhydrous sodium sulfate) and concentrated in vacuo to afford the resolved dextrorotatory amine 9 (51 mg, 7.3% overall yield) as a colorless amorphous solid. TLC Rf (methylene chloride/methanol/concentrated aqueous ammonia=9:1:0.1 in volume; iodoplatinate spray: 1; $[\alpha]_D^{20}$+7.86 (c=1.22, methylene chloride).

EXAMPLE 13

Coupling Method A

Racemic (7S*,9aS*)-2-(Benzo[d]isoxazol-3-yl)-perhydro-7-(2-(3,3-tetramethyteneglutarimido)-ethyl)-1H-pyrido[1,2-e]pyrazine A mixture consisting of racemic amine title product of Example 10 (465 mg, 1.54 mol) and 3,3-tetramethylene gluteric anhydride (290 mg, 1.70 mmol, Aldrich Chemical Co.) in xylenes (6 ml, boiling range 139°–144° C.) was refluxed vigorously for 18 hours. The xylene solution was carefully decanted from the insoluble tar formed during the reaction period; and the tar was then thoroughly extracted with a fresh portion of xylenes (4 ml). The combined xylene portions were concentrated in vacuo to an oil (0.65 g). Rash chromatography of the entire sample (20 g silica gel, 32–63 mesh; eluting initially with ethyl acetate/hexane=1:1; with decreasing hexane content of the eluting system during the course of the chromatography, leading to pure ethyl acetate elution at its completion)afforded the present title compound (75 mg, 10.8% yield) as a colorless amorphous solid. TLC Rf (ethyl acetate elution, potassium permanganate spray): 0.25.

EXAMPLE 14

Coupling Method B

Racemic (7S*,9aS*)-2-(Benzo[d]isoxazol-3-yl)-perhydro-7-(2-(3,3-trimethyleneglutarimido)-ethyl)-1H -pyrido[1,2-a ]pyrazine A mixture consisting of racemic amine product of Example 10 (98 mg, 0.326 retool)and 3,3-tetramethylene gluteric arthydride (55 mg, 0.359 mmol) in "xylenes" (4.0 ml, boiling range 139°–144° C.) was stirred and heated at 150° C. for 15 minutes. The xylene solvent was carefully removed in vacuo (considerable frothing occurs) to afford the crude intermediate non-cyclized, acid-amide as an amber solid. Dehydrative cyclization of the entire sample was carried out in acetic anydride (1.0 ml) by heating the reaction mixture at 100°–110° C. for 2.5 hours. Concentration of the mixture in vacuo afforded a solid residue which was crystallized from isopropanol to afford 48.0 mg (33.7% yield) of the present title compound; m.p. 163.9°–165.3° C. $^{13}$CNMR (CDCl$_3$) delta 171.7, 164.0, 161.0, 129.5, 122.2 (2), 116.0, 110.5, 61.3, 60.2, 54.2, 53.7, 48.2, 44.9, 37.4, 35.1, 34.1, 32.7, 31.1, 30.4, 29.3, 14.7.

EXAMPLE 15

Coupling Method B

Optically Active (7S,9aS)-2-(Benzo[d]isoxazol-3-yl) perhydro-7-(2-(3,3-tetramethyleneglutar-imido) ethyl)-1H-pyrido[1,2-a]pyrazine A mixture consisting of 7S,9aS-(−)-amine title product of Example 11 (1.53 g, 5.09 retool) and 3,3-tetramethylene gluteric anhydride (0.94 g, 5.50 mmol, Aldrich Chemical Co.) in xylenes (60 ml, boiling range 138.9°–143.9° C.) was stirred and heated at 150° C. for 15 minutes. The xylenes were carefully removed in vacuo (considerable frothing occurs) to afford the crude non-cyclized acid-amide as an amber solid [TLC Rf (methylene chloride/methanol=9:1 in volume; iodoplatinate spray): 0.45] sufficiently pure for imide formation without purification. The entire sample was stirred and heated in acetic anhydride (42 ml) at 100°–110° C. for 2.5 hours. The reaction mixture was concentrated in vacuo to afford a solid residue which was partitioned in a well-stirred methylene chloride/water (60 ml and 50 ml, respectively) mixture with the pH adjusted to 9.5 (saturated aqueous sodium carbonate). The phases were separated, and the aqueous phase was extracted with an equal volume of fresh methylene chloride. Concentration in vacuo of the combined organic extracts afforded a yellow solid. Flash chromatography of the entire sample (30 g silica gel, 32–63 mesh; eluting initially with methylene chloride and then adding methanol to increase the polarity of the eluting system to a final methylene chloride/methanol ratio of 97:3 in volume) afforded the pure EFLC inspection in a variety of eluting systems; potassium permanganate spray) title compound as a colorless amorphous solid (1.40 g, 61% yield). $[\alpha]_D^{20}$ –4.6 (c=2.3, methylene chloride). TLC Rf (ethyl acetate; potassium permanganate spray): 0.25. MS m/z 450.2639 (M, $C_{26}H_{34}O_3N_4$). $^{13}$CNMR (CDCl$_3$) delta 172.1, 164.0, 161.1, 129.5, 122.2 (2), 116.2, 110.5, 61.3, 60.2, 54.2, 53.7, 48.2, 44.9, 39.5, 37.5, 37.4, 34.2, 32.6, 30.4, 29.3, 24.2.

A 230 mg sample of the amorphous product was twice crystallized from isopropanol (2 ml portions), affording 150 mg (65.2% yield) of colorless crystals; m.p. 157°–158° C. The spectroscopic properties, including optical rotation, of the amorphous and crystalline material were identical. An enantioselective, quantitative, High Performance Liquid Chromatography (HPLC) assay was developed using a Chiral Type AGP ($\alpha_1$-glycoprotein) column (mobile phase: 0.01M aqueous dihydrogen potassium phosphate/ acetonitrile/dimethyloctylamine=900:100:0.2; flow rate: 0.9 ml/minute; ultraviolet HPLC detector at 215 nm wavelength). By this assay, the optical purity of title compound product was found to be>95%.

EXAMPLE 16

Mesylate Salt

A 69.6 mg (0.154 mmol) amorphous title product of Example 15 was dissolved in ethyl acetate (1 ml). Methanesulfonic acid (16.6 mg, 0.170 mmol: 98%, Aldrich Chemical Co.) was added, and the resulting solution was stirred for 2 hours at ambient temperature, during which time, a heavy crystalline mass formed. The product was filtered, washed with diethyl ether and dried in vacuo to afford the monomesylate salt of the title product of Example 12 as colorless needles, 54 mg (63.9% yield); m.p. 211°–212° C. $[\alpha]_D^{20}$ –3.7 (c=2.1, methylene chloride). $^{13}$CNMR (CDCl$_3$) delta 172.5, 164.2, 159.7, 130.2, 123.1, 121.4, 115.3, 110.7, 61.4, 59.6, 52.3, 50.5, 45.7, 44.6, 39.6, 37.5, 36.0, 31.4, 31.1, 28.6, 26.1,24.2.

The experiment was repeated on a larger scale (468 mg, 1.04 mmol) to afford the identical crystalline product (500 mg) in 88% yield.

The optical purity of this monomesylate salt was determined to be≧98% by the quantitative enantioselective HPLC assay described in Example 15.

EXAMPLE 17

Optically Active (7R,9aR)-2-(Benzo[d]isoxazol-3-yl)perhydro-7-(2-(3,3-tetramethyleneglutarimido) ethyl)-1H-pyrido[1,2-a]pyrazine By the method of Example 15, dextrorotatory amine product of Example 12 (25 mg, 0.083 mmol) was converted into present title product (15 mg, 40% yield) isolated as a colorless amorphous solid. TLC Rf (ethyl acetate, potassium permanganate spray): 0.25. $[\alpha]_D^{20}$+3.63(c=0.77, methylene chloride). The optical purity of the title compound was found to be≧95% by the HPLC enantioselective assay described in Example 15.

EXAMPLE 18

Racemic (7S*,9aS*)-2-(Benzo[d]isoxazol-3-yl)-perhydro-7-(2-cyclohexylmethylcarbonylamino)-ethyl)-1H-pyrido[1,2-a]pyrazine To a well-stirred solution of cyclohexylacetic acid (35 mg, 0.25 mmol, Aldrich Chemical Co.) in anhydrous methylene chloride (2 ml), 1-hydroxybenzotriazole (37 mg, 0.25 mmol), 1-cyclohexyl-3-(2-morpholinoethyl)carbodiimide metho-p-toluenesulfonate (145 mg, 0.34 mmol, Aldrich Chemical Co.), and amine title product of Example 7 (51 mg, 0.17 mmol) were added, and the resulting mixture was stirred at ambient temperature for 18 hours. The solvent was removed in vacuo, and the residue was partitioned in a weft-stirred methylene chloride/water mixture (10 ml of each) with the pH adjusted to 9 (saturated aqueous sodium carbonate). The separated organic phase was concentrated in vacuo to a solid. Rash chromatography of the entire sample (2.0 g silica gel, 32–63 mesh; eluting with methylene chloride/methanol=97:3 in volume) afforded the present title compound as a colorless amorphous solid, 12 mg (17% yield). TLC Rf (methylene chloride/methanol=9:1 in volume, potassium permanganate spray): 0.40; MS m/z 424.2854 (M, $C_{25}H_{36}O_2N_4$).

EXAMPLE 19

Racemic (7S*,9aS*)-2-(Benzo[d]isoxazol-3-yl) perhydro-7-(2-(2-thenoylamino)-ethyl)-1H-pyrido[1, 2-a ]pyrazine A solution consisting of amine title product of Example 10 (100 mg, 0.33 mmol), triethylamine (0.051 ml, 37.2 mg, 0.37 mmol) and 2-thenoyl chloride (0.039 ml, 53.5 mg, 0.37 mmol, Aldrich Chemical Co.) in anhydrous methylene chloride (5.0 ml) was stirred at ambient temperature for 1 hour. An equal volume of water was added, and the pH of the well-stirred mixture was adjusted to 9.5 (aqueous saturated sodium carbonate). The phases were separated, and the aqueous portion was extracted with an equal volume of fresh methylene chloride. The combined organic extracts were washed with water (10 ml), dried (anhydrous sodium sulfate) and concentrated in vacuo to a solid. Flash chromatography of the entire sample (3.8 g silica gel, 32–63 mesh; eluting with ethyl acetate) afforded the title compound as a colorless amorphous solid, 16.8 mg (12.3% yield). TLC Rf (methylene chloride/methanol=9:1 in volume; potassium permanganate spray): 0.51. HRMS 410.1759 corresponding to mass ion $C_{22}H_{26}N_4O_2S$.

EXAMPLE 20

Racemic (7R*,9aS*)-2-(Benzo[d]isoxazol-3-yl)-perhydro-7-((3,3-tetramethyleneglutarimido)-methyl)-1H-pyrido[1,2-a]pyrazine 3,3-Tetramethyleneglutarimide (18.3 mg, 0.11 mmol) was added to a well-stirred suspension of sodium hydride (4.4 mg of 60% sodium hydride mineral oil dispersion; 2.64 mg, 0.11 mmol of sodium hydride) in anhydrous N,N-dimethylformamide (DMF, 0.5 ml). The reaction was stirred and heated to 60° C. under dry nitrogen for 20 minutes. A solution of mesylate title product of Example 8 (20 mg, 0.55 mmol) in anhydrous DMF (1.0 ml) was added and the resulting mixture was stirred at 100° C. for 6 hours. The solvent was removed in vacuo, and the residue was partitioned in a well-stirred methylene chloride/water mixture (15 ml of each) with the pH adjusted to 10 (saturated aqueous sodium carbonate). The organic phase was separated, treated with activated charcoal and filtered, dried (anhydrous sodium sulfate) and, finally, concentrated in vacuo to a colorless amorphous solid. Crystallization of the entire sample from isopropanol afforded 13.2 mg (55% yield) of the present title compound; m.p. 208–209° C. HRMS 436.2466 corresponding to mass ion $C_{25}H_{32}N_4O_3$.

EXAMPLE 21

Racemic (7R*,9aS*)-7-(Azidomethyl)-2-(benzo[d]isoxazol-3-yl)perhydro-1H-pyrido[1,2-a]pyrazine A mixture consisting of mesylate title product of Example 8 (473 mg, 1.29 mmol) and sodium azide (170 mg, 2.58 mmol) in anhydrous N,N-dimethylformamide (5.0 ml) was stirred at 100° C. for 17 hours. The heterogeneous reaction mixture was concentrated in vacuo to an oily residue which was then partitioned into a well-stirred methylene chloride/water mixture (20 ml of each) with the pH adjusted to 11.5 (saturated aqueous sodium carbonate). The organic phase was separated, dried over anhydrous sodium sulfate and concentrated in vacuo to afford present title product (in which the 7- and 9a-hydrogen atoms are trans) as a light yellow amorphous solid (370 mg, 91.2% yield). TLC Rf (ethyl acetate/methanol/concentrated aqueous ammonia= 9:2:0.2 in volume; potassium permanganate spray): 0.78.

By the same method, the 8R*,9aS*)-8-(methanesulfonyloxymethyl) title product of Example 39 is converted to the corresponding (8R*,9aS*)-8-(aminomethyl) derivative in which the 8- and 9a- hydrogen atoms are cis.

EXAMPLE 22

Racemic (7S*,9aS*)-7-(Aminomethyl)-2-(benzo[d]isoxazol-3-yl)perhydro-1H-pyrido[1,2-a]pyrazine A solution of azide title product of Example 21 in an ethanol/methanol mixture (2 ml and 1 ml, respectively) was hydrogenated on a Parr apparatus (50 psi, 26 mg of 5% palladium-on-carbon catalyst) for 2.5 hours. The catalyst was filtered under nitrogen, and the resulting filtrate was concentrated in vacuo to afford present title product as a colorless amorphous solid (50 mg, 99% yield). TLC Rf (ethyl acetate/methanol/concentrated aqueous ammonia= 9:2:0.2 in volume, potassium permanganate spray): 0.15. $^{13}$CNMR (CDCl$_3$)delta 164.0, 161.0, 129.5, 122.3, 122.2, 116.1, 110.4, 60.3, 59.6, 54.2, 53.7, 48.2, 46.4, 39.6, 29.0, 28.2.

By the same method, the corresponding 8-(azidomethyl) derivative is converted to the corresponding 8-(aminomethyl) derivative.

EXAMPLE 23

Racemic (7R*,9aS*)-2-(Benzo[d]isoxazol-3-yl)-perhydro-7-((3,3-tetramethyleneglutarimido)-methyl)-1H-pyrido[1,2-a]pyrazine A mixture consisting of amine title product of Example 22 (31 mg, 0.11 mmol) and 3,3-tetramethylene glutaric arthydride (20 mg, 0.12 mmol, Aldrich Chemical Co.)in xylenes (1.0 ml, boiling range 139°–144° C.) was stirred and heated at 105° C. for 10 minutes. After cooling to ambient temperature, the xylenes were carefully removed in vacuo (considerable frothing occurs) to afford acid-amide intermediate as a colorless solid [TLC Rf (methylene chloride/methanol=9:1 in volume; potassium permanganate spray): 0.39]used for amide formation without purification. The entire sample was stirred and heated at 105° C. in acetic anhydride (2.0 ml) for 3 hours. The excess acetic anhydride was removed in vacuo to afford a solid residue which was then partitioned in a well-stirred methylene chloride/water (10 ml and 5 ml, respectively) mixture with the pH adjusted to 9 (saturated aqueous sodium carbonate). The organic phase was dried (anhydrous sodium sulfate) and concentrated in vacuo to a solid (33 mg). Flash chromatography of the entire sample (550 mg of silica gel, 32–63 mesh; eluting initially with methylene chloride and then increasing the polarity of the eluting system by adding methanol to a final methylene chloride/methanol ratio of 98:2 in volume) afforded the title compound 19 as a colorless amorphous solid (16.4 mg, 34.8% yield). TLC Rf (methylene chloride/methanol=9:1 in volume; potassium permanganate spray): 0.42. HRMS m/z 436.2466 (M, $C_{25}H_{32}O_3N_4$). $^{13}$CNMR (CDCl$_3$) delta 172.4, 164.0, 161.1,129.5, 122.2, 122.1,116.2, 110.5, 60.0, 59.6, 54.3, 53.7, 48.2, 44.9, 42.8, 39.4, 37.7, 35.9, 29.1, 28.4, 24.3.

A sample of the pure amorphous product readily crystallized from isopropanol (m.p. 208°–209° C.). The crystalline product was identical in all respects to that prepared by the method of Example 20.

EXAMPLE 24

Racemic (7S*,9aS*)-7-(Cyclohexylmethyl-carbonylaminomethyl)-2-(benzo[d]isoxazol-3-yl)perhydro-1H-pyrido[1,2-a]pyrazine To a well-stirred solution of cyclohexylacetic acid (23 mg, 0.16 mmol. Aldrich Chemical Co.) in anhydrous methylene chloride (1 ml), 1-hydroxybenzo-triazole (25 mg, 0.16 mmol), 1-cyclohexyl-3-(2-morpholinoethyl)carbodiimide metho-p-toluenesulfonate (100 mg, 0.25 mmol), and amine title product of Example 22 (36 mg, 0.13 mmol) were added. The resulting mixture was stirred at ambient temperature for 18 hours. The solvent was removed in vacuo, and the residue was partitioned in a well-stirred methylene chloride/water mixture (10 ml of each) with the pH adjusted to 9 (saturated aqueous sodium carbonate). The separated organic phase was concentrated in vacuo to a solid. Flash chromatography of the entire sample (2.0 g silica gel, 32–63 mesh; eluting with ethyl acetate:methanol=9:1 in volume) afforded the present title compound as a colorless amorphous solid, 10 mg (19.5% yield). TLC Rf (methylene chloride/methanol= 9:1 in volume; potassium permanganate spray): 0.43. HRMS 410.2684 corresponding to mass ion $C_{24}H_{34}N_4O_2$.

EXAMPLE 25

Racemic (7S*,9aS*)-2-(Benzo[d]isoxazol-3-yl)-7-(4-(4-fluorobenzoyl)piperidinomethyl)-perhydro-1H-pyrido[1,2-a]pyrazine To a solution of 4-(p-fluorobenzoyl)piperidine (11.9 mg, 0.058 mmol) in methylisobutylketone (0.2 ml), sodium carbonate (15.2 mg, 0.14 mmol), potassium iodide (1 mg), and a solution of mesylate title product of Example 8 (21 mg, 0.058 mmol) in methylisobutylketone (0.3 ml) were added, and the resulting mixture was refluxed for 4 hours.

The solvent was removed in vacuo, and the residue was dissolved in a well-stirred methylene chloride/water (20 ml and 10 ml, respectively) mixture (pH 11). The phases were separated, and the aqueous portion was extracted twice with 25 ml of fresh methylene chloride. The combined organic extracts were treated with activated charcoal, dried (anhydrous sodium sulfate) and concentrated in vacuo to a colorless solid. Crystallization of the entire sample from isopropanol afforded present title compound, 13.9 mg, 56.7% yield; m.p. 179°–181° C. TLC Rf (ethyl acetate/methanol=9:1 in volume; potassium permanganate spray): 0.17.

EXAMPLE 26

Racemic (7S*,9aS*)-2-(Benzo[d]isoxazol-3-yl)perhydro-7-(2,2-di(methoxycarbonyl)-ethyl)-1H-pyrido[1,2-a]pyrazine To a solution of dimethyl malonate (2.054 g, 15.5 mmol) in anhydrous N,N-dimethylformamide (80 ml), sodium hydride (0.77 g of 60% sodium hydride in mineral oil dispersion; 462 mg, 19.3 mmol sodium hydride) was added, and the stirred mixture was heated at 55° C. for 1 hour. Mesylate title product of Example 8 (5.44 g, 14.9 mmol) was added, and the resulting mixture was stirred and heated at 100° C. for 42 hours. The solvent was removed in vacuo leaving a solid residue which was then dissolved in a well-stirred methylene chloride/ saturated aqueous bicarbonate biphasic mixture (150 ml of each; pH=8.9). The organic phase was separated, washed successively with equal volumes of water and brine, dried (anhydrous sodium sulfate)and concentrated in vacuo to a solid. The entire sample was taken up in warm ethyl acetate. Hexane was then added until the solution became turbid. Within 3 hours standing at ambient temperature, present title product crystallized (2.60 g, 43.5% yield; m.p. 134–138° C.). TLC Rf (ethyl acetate, potassium permanganate spray): 0.36.

EXAMPLE 27

Racemic (7S*,9aS*)-2-(Benzo[d]isoxazol-3-yl)perhydro-7-(3-(methanesulfonyloxy)-propyl)-1H-pyrido[1,2-a]pyrazine Title dimethylmalonate derivative of Example 26 (0.65 g, 1.62 mmol) was vigorously refluxed in concentrated hydrochloric acid for 3 hours. The pH of the reaction mixture (cooled to ambient temperature) was adjusted to 6.8 by dropwise addition of 10% aqueous lithium hydroxide. Concentration of the mixture in vacuo afforded the intermediate, solid, crude lithium salt of racemic (7S*,9aS*)-7-(2-carboxyethyl)perhydro-2-(benzo[d]isoxazol-3-yl)-1H-pyrido[1,2-a]pyrazine. The entire sample was stirred for 18 hours in methanol-concentrated sulfuric acid (7.0 and 0.12 ml, respectively). Concentration in vacuo afforded an oily residue which was dissolved in a ethyl acetate/saturated aqueous sodium bicarbonate (25 ml of each; pH=7.8) biphasic mixture. The organic phase was separated and concentrated in vacuo to an oil (0.48 g). Flash chromatography of the entire sample (25 g of silica gel, 32–63 mesh, elution initially with methylene chloride and finally with methylene chloride/methanol=97:3 in volume) afforded the corresponding pure methyl ester (0.23 g, 41.8% yield) as a colorless oil. TLC Rf (ethyl acetate, potassium permanganate spray): 0.20. $^{13}$CNMR (CDCl$_3$) delta 174.0, 164.0, 161.0, 129.5, 122.3, 122.1, 116.1, 110.5, 61.3, 60.2, 54.1, 53.7, 51.6, 48.2, 35.6, 31.5, 30.2, 29.5, 29.2.

A reaction mixture consisting of this monomethyl ester (23 mg, 0.07 mmol) and lithium aluminum hydride (0.167 ml of a 1.0M solution in tetrahydrofuran; 0.17 mmol of lithium aluminum hydride) in anhydrous tetrahydrofuran (0.5 ml) was refluxed for 4 hours. The reaction was cooled to ambient temperature and quenched with a methanol (7 drops)/tetrahydrofuran (5 ml) solution. The inorganics were filtered, and the filtrate was concentrated in vacuo to afford the corresponding alcohol product, racemic (7S*,9aS*)-2-(benzo-[d]isoxazol-3-yl)-perhydro-7-(3-hydroxypropyl)-1H-pyrido[1,2-a]pyrazine, as a colorless amorphous solid (15.9 mg, 75.4% yield). TLC Rf (methylene chloride/methanol=9:1 in volume, potassium permanganate spray): 0.35. $^{13}$CNMR (CD$_3$OD) delta 165.1, 162.2, 131.2, 123.8, 123.7, 116.9, 111.0, 63.0, 62.5, 61.7, 55.0, 54.3, 48.9, 36.7, 31.6, 31.4, 30.6, 29.9.

By the method of Example 8, this alcohol (20 mg, 0.06 mmol) was converted to present title mesylate ester isolated as an amorphous solid in quantitative yield. TLC Rf (ethyl acetate, potassium permanganate spray): 0.17.

EXAMPLE 28

Racemic (7R*,9aS*)-2-(6-Chlorobenzo[d]-isoxazol-3-yl)perhydro-7-(hydroxymethyl)-1H-pyrido[1,2-a]pyrazine By the method of Example 7, the alcohol-amine title product of Example 6 (203 mg, 1.19 mmol) and 3,6-dichlorobenzo[d]isoxazole were converted into present title product (206 mg, 53.8% yield) isolated as a pale yellow amorphous solid. In this product the 7-and 9a-hydrogen substitutents are trans. TLC Rf (methylene chloride/methanol=9:1 in volume; potassium permanganate spray): 0.41. $^{13}$CNMR (CDCl$_3$) delta 164.2, 160.6, 136.1, 123.3, 122.8, 114.9, 110.8, 65.9, 60.2, 58.7, 54.1, 53.4, 48.0, 39.0, 28.8, 26.7.

EXAMPLE 29

Racemic (7R*,9aS*)-2-(6-Chlorobenzo[d]isoxazol-3-yl)perhydro-7-((3,3-tetramethyleneglutar-imido)methyl)-1H-pyrido[1,2-a]pyrazine.

By the methods of Examples 8 and 20, the alcohol title product of Example 26 (66 mg, 0.165 mmol) was converted to present title product (13.7 mg, 17.6% yield)and isolated as a colorless solid. TLC Rf (methylene chloride/methanol=9:1 in volume; potassium permanganate spray): 0.64. $^{13}$CNMR (CDCl$_3$) delta 172.4, 164.4, 160.9, 136.0, 123.2, 122.7, 115.1, 110.8, 59.9, 59.5, 54.2, 53.6, 48.2, 44.9, 42.8, 39.4, 37.7, 35.9, 29.0, 28.3, 24.3.

EXAMPLE 30

Racemic (7B*,9aS*)-2-(Benzyloxycarbonyl)-perhydro-7-(hydroxymethyl)-1H-pyrido[1,2-a]pyrazine To a solution of the title product of Example 6 (640 mg, 3.76 mmol)in acetone/water (6.3 ml and 2.2 ml, respectively), a solution of benzylchloroformate (0.61 ml, 729 mg, 4.27 mmol) in acetone (2,0 ml) was added dropwise over several minutes while maintaining the pH of the mixture at 9.5 by intermittent dropwise addition of saturated aqueous sodium carbonate. After completing the addition, the reaction was stirred for 5 minutes at ambient temperature. The acetone solvent was removed in vacuo, ethyl acetate (60 ml) and water (30 ml) were added, and the pH of the well-stirred mixture was adjusted to 9.5 (sodium carbonate). The separated organic phase was dried

19

(anhydrous sodium sulfate)and concentrated in vacuo to an oil (940 mg). Rash chromatography of the entire sample [10 g, silica gel, 32–63 mesh, eluting initially with ethyl acetate (100 mg), followed by ethyl acetate/methanol (100 ml, 97:3 in volume) and finally ethyl acetate/methanol (200 ml, 90:10 in volume)]afforded the present title compound as a colorless oil, 350 mg (30.6% yield). TLC Rf (ethyl acetate/methanol/concentrated aqueous ammonia=9:2:0.2 in volume): 0.63.

EXAMPLE 31

Racemic (7R*,9aS*)-2-(Benzyloxycarbonyl)-perhydro-7-((3,3-tetramethyleneglutarimido)-methyl-1H-pyrido[1,2-a]pyrazine To a chilled (5° C.) and stirred solution of N-carbobenzyloxy protected intermediate of Example 30 (328 mg, 1.07 mmol) and triethylamine (0.164 ml, 1.18 mmol) in methylene chloride (7 ml), a solution of methane-sulfonyl chloride (0.087 ml, -1.13 mmol) was added dropwise. The reaction mixture was stirred at ambient temperature for 15 minutes. Methylene chloride (10 ml)and water (15 ml) were added, and the pH of the well-stirred mixture was adjusted to 9.5 (1N aqueous sodium hydroxide). The organic phase was separated, washed with three equal volumes of water, dried (anhydrous sodium sulfate) and concentrated in vacuo to afford the crude mesylate ester intermediate. The entire sample was dissolved in anhydrous N,N-dimethylformamide (DMF, 2.0 ml), and the resulting solution was added to a DMF (3.0 ml) solution of sodium 3,3-tetramethylene glutarimide prepared from sodium hydride (47 mg of 60% sodium hydride in mineral oil dispersion, 28.2 mg, 1.18 mmol of sodium hydride) and 3,3-tetraethylene glutarimide (198 mg, 1.18 mmol, Aldrich Chemical Co.). The mixture was stirred and heated at 90° C. for 19 hours. Concentration in vacuo afforded an oil, which was dissolved in a well-stirred ethyl acetate/water mixture (30 ml of each) with the pH adjusted to 2.0 (6N concentrated hydrochloric acid). The phases were separated, and the aqueous extract was stirred with a fresh equal volume portion of ethyl acetate with pH adjusted to 8.5 (saturated aqueous sodium carbonate). The separated organic phase was concentrated in vacuo to an oil. NMR inspection showed the desired product contaminated with residue 3,3-tetramethylene glutarimide which was removed by an additional basic work-up (methylene chloride/water, 30 ml of each, with pH adjusted to 9.0 with sodium carbonate). In vacuo concentration of the anhydrous sodium sulfate-dried organic extract afforded present title compound as a colorless viscous oil, 230 mg (47.9% yield). TLC Rf (methylene chloride/methanol=9:1; potassium permanganate spray): 0.60.

20

EXAMPLE 32

Racemic (7R*,9aS*)-7-((3,3-tetramethyleneglutar-imido)methyl)perhydro-1H-pyrido[1,2-a]pyrazine A solution of the title product of Example 31 (230 mg, 0.51 mmol) in an ethanol/methanol mixture (10 ml and 2 ml, respectively) was hydrogenated on a Parr apparatus (50 psig hydrogen pressure over 100 mg of 20% palladium hydroxide-on-carbon catalyst)for 2 hours. The catalyst was filtered under nitrogen, and the resulting filtrate was concentrated in vacuo to afford present title compound as a colorless viscous oil, 150 mg (92% yield).

EXAMPLE 33

Racemic (7R*,9aS*)-2-(Benzo[d]isothiazol-3-yl)-perhydro-7-((3,3-tetramethyleneglutarimido)-methyl-1H-pyrido[1,2-a]pyrazine A mixture consisting of the title product of Example 32 (90 mg, 0.28 mmol), 3-chloro-1,2-benzisothiazole (95.2 mg, 0.56 mmol) and sodium carbonate (60 mg, 0.56 mmol)in isoamyl alcohol (1.0 ml) was stirred and heated at 110° C. for 1 hour. The mixture was cooled to 50° C. and additional 3-chlorobenzisoythiazole thiazole (95.2 mg, 0.56 mmol) was added. The reaction was then stirred and heated at 120° C. for three hours. After cooling to ambient temperature, methylene chloride (10 ml) was added, the resulting mixture was filtered, and the filtrate was concentrated in vacuo to an oil. Flash chromatography of the entire sample (3 g silica gel, 32–63 mesh, eluting initially with ethyl acetate/hexane, then with ethyl acetate, and finally with ethyl acetate/methanol/concentrated aqueous ammonia=9:2:0.1 in volume) afforded the present title compound as a colorless amorphous solid, 25 mg (19.7% yield). TLC Rf (ethyl acetate/hexane=1:1 in volume): 0.18.

EXAMPLE 34

Using the methods of the preceding Examples additional trans-7-substituted compounds of the formula

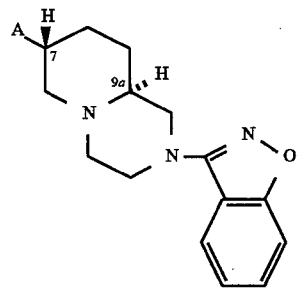

were prepared as follows:

| (±)/(−) | A | Examples[a] | Yield | Properties[b] |
|---|---|---|---|---|
| (±) | ![structure] H—CH₂— | 5/22 | 29% | Rf 0.63(9:1 CH$_2$Cl$_2$: MeOH) HRMS 412.2483 |

-continued

| (±)/(−) | A | Examples[a] | Yield | Properties[b] |
|---|---|---|---|---|
| (±) | (bicyclic dimethyl dicarboximido-N-CH₂— group) | 5/17 | 28% | Rf 0.53(9:1 CH₂Cl₂:MeOH) HRMS 450.2635 |
| (±) | (norbornene dicarboximido-N-CH₂— group) | 5/17 | 28% | Rf 0.26(ethyl acetate) HRMS 432.2141 |
| (±) | (bicyclic sulfonamide N-CH₂— group) | 5/17 | 13% | Rf 0.45(ethyl acetate) HRMS 484.2498 |
| (±) | (cyclopentane-spiro thiazolidinedione N-CH₂— group) | 5/17 | 73% | Rf 0.76(ethyl acetate) HRMS 440.1849 |
| (+) | 2-(3,3-tetramethylene-glutarimido)ethyl | 9/11,12 | 55% | Rf 0.25(ethyl acetate) HRMS 450.2639 |
| (±) | 3-(3,3-tetramethylene-glutarimido)propyl | 24/17 | 24% | Rf 0.47(9:1 CH₂Cl₂:(MeOH) |
| (±) | 2-(3,3-pentamethylene-glutarimido)ethyl | 7/11,12 | 20% | Rf 0.61(9:1 CH₂Cl₂:MeOH) HRMS 464.2792 |
| (±) | 2,2-dimethylglutar-imido)methyl | 19/11,12 | 14% | Rf 0.39(9:1 CH₂Cl₂:MeOH) HRMS 410.2306 |
| (±) | 2-(cyclopentyl-carbonylamino)ethyl | 7/21 | 22% | Rf 0.46(9:1 CH₂Cl₂:MeOH) HRMS 396.2523 |
| (−) | 2-(cyclopentyl-carbonylamino)ethyl | 8/16 | 61% | Rf 0.43(9:1 CH₂Cl₂:MeOH) HRMS 396.2528 $[\alpha]_D^{20} = -3.63$ (c = 1.1, CH₂Cl₂) |
| (−) | 2-(cyclopentylacetyl-amino)ethyl | 8/15 | 29% | 0.49(9:1 CH₂Cl₂:MeOH) HRMS 410.2692 |
| (−) | 2-(cyclohexyl-carbonylamino)ethyl | 8/16 | 24% | Rf 0.45(9:1 CH₂Cl₂:MeOH) HRMS 410.2695 $[\alpha]_D^{20} = -2.92$ (c = 0.41, CH₂Cl₂ |
| (±) | (norbornyl-CH₂-C(O)-NH-propyl group) | 7/15 | 16% | Rf 0.6(9:1 CH₂Cl₂:MeOH) HRMS 436.2834 |
| (±) | 2-((phenylacetyl)-amino)ethyl | 7/15 | 14% | Rf 0.39(9:1 CH₂Cl₂:MeOH) HRMS 418.2363 |
| (±) | 2-cycloheptylcarbonyl-amino)ethyl | 7/15 | 27% | Rf 0.47(9:1 CH₂Cl₂:MeOH) HRMS 424.2829 |
| (−) | 2-cycloheptylcarbonyl-amino)ethyl | 8/15 | 62% | Rf 0.47(9:1 CH₂Cl₂:MeOH) HRMS 424.2821 $[\alpha]_D^{20} = -3.14$ (c =1.05, CH₂Cl₂) |
| (±) | 2-cyclobutylcarbonyl-amino)ethyl | 7/15 | 17% | Rf 0.41(9:1 CH₂Cl₂:MeOH) HRMS 382.2346 |

-continued

| (±)/(−) | A | Examples[a] | Yield | Properties[b] |
|---|---|---|---|---|
| (±) | 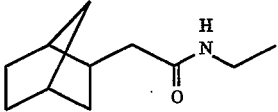 | 19/21 | 13% | Rf 0.56(9:1 CH$_2$Cl$_2$: MeOH) HRMS 422.2695 |
| (±) | 2-(3-cyclohexyl-propionylamino)ethyl | 7/15 | 37% | Rf 0.46(9:1 CH$_2$Cl$_2$: MeOH) HRMS 438.3002 |
| (±) | 2-(3-cyclopentyl-propionylamino)ethyl | 7/15 | 14% | Rf 0.36(9:1 CH$_2$Cl$_2$: MeOH) HRMS 424.2852 |

[a]Source of Starting Material/Coupling Method(s)
[b]Rf values are for thin layer chromatography (TLC) with KMnO$_4$ spray;
HRMS = high resolution mass spectrum, observed values are for the mass ion and and are very close to theoretical.

I claim:

1. A process for the preparation of a trans piperidine derivative of the formula

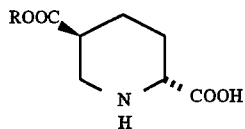 (I)

wherein R is a (C$_1$–C$_4$)alkyl which comprises contacting a corresponding cis-substituted piperidine derivative of the formula

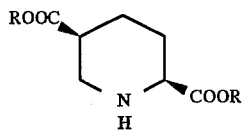 (II)

wherein R is defined as above, with an aldehyde in a carboxylic acid of the formula R$^1$COOH, wherein R$^1$ is hydrogen or (C$_1$–C$_3$)alkyl; and separating said trans derivative of the formula (I) from the resulting mixture.

2. A process of claim 1 wherein the aldehyde is salicylaldehyde.
3. A process of claim 1 wherein R is methyl.
4. A process of claim 2 wherein R is methyl.
5. A process of claim 1 wherein R$^1$ is methyl.
6. A process of claim 2 wherein R$^1$ is methyl.
7. A process of claim 3 wherein R$^1$ is methyl.
8. A process of claim 4 wherein R$^1$ is methyl.
9. A process for the preparation of a trans-piperidine derivative of the formula

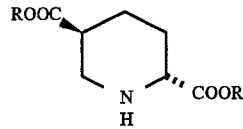

wherein R is (C$_1$–C$_3$)alkyl, which comprises the steps of:
(a) contacting a corresponding cis-substituted piperidine derivative of the formula

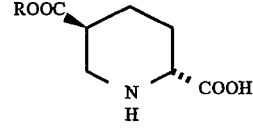

wherein R is defined as above, with an aldehyde in a carboxylic acid R$^1$COOH, wherein R$^1$ is hydrogen or (C$_1$–C$^3$)alkyl, to form a mixture of trans and cis compounds of the formulas

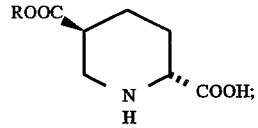

(b) conventionally esterifying said mixture of compounds of the formulas (I) and (IV) to form a mixture of said trans and cis derivatives of the above formulas (II) and (III); and (c) separating said trans derivative of the formula (II) from the mixture.

10. A process of claim 9 wherein the aldehyde is salicylaldehyde.
11. A process of claim 9 wherein R is methyl.
12. A process of claim 10 wherein R is methyl.
13. A process of claim 9 wherein R$^1$ is methyl.
14. A process of claim 10 wherein R$^1$ is methyl.
15. A process of claim 1 wherein R$^1$ is methyl.
16. A process of claim 12 wherein R$^1$ is methyl.

* * * * *